United States Patent [19]

Bayer et al.

[11] 3,960,830

[45] June 1, 1976

[54] POLYALKYLENE GLYCOLS USED FOR THE PREPARATION OF PEPTIDES

[75] Inventors: Ernst Bayer; Manfred Mutter, both of Tubingen, Germany

[73] Assignee: Hoechst Aktiengesellschaft, Frankfurt am Main, Germany

[22] Filed: Dec. 4, 1974

[21] Appl. No.: 529,519

[30] Foreign Application Priority Data

Dec. 6, 1973 Germany............................ 2360794

[52] U.S. Cl............................................ 260/112.5 R
[51] Int. Cl.².................................... C07C 103/52
[58] Field of Search ............................... 260/112.5

[56] References Cited
UNITED STATES PATENTS 3,502,545  3/1970  Westman et al. ................. 260/112.5

3,645,852  2/1972  Axen et al. ...................... 260/112.5

OTHER PUBLICATIONS

Bayer et al.: Nature, 237, pp. 512–513, (1972).

*Primary Examiner*—Lewis Gotts
*Assistant Examiner*—Reginald J. Suyat
*Attorney, Agent, or Firm*—Curtis, Morris & Safford

[57] ABSTRACT

A process for the synthesis of peptides in a liquid phase wherein the peptide product, and intermediates in the peptide synthesis, are bound to a polyalkylene glycol polymer and wherein the polymer-bound peptide is separated from the liquid phase, e.g. for purposes of isolation or purification, by crystallizing the polymer-bound peptide.

2 Claims, No Drawings

POLYALKYLENE GLYCOLS USED FOR THE PREPARATION OF PEPTIDES

The present invention relates to a process for the preparation of peptides.

It is known that polyethylene glycol can be used as an ester component in peptide chemistry [Nature 237, 512 – 513 (1972)]. For this purpose, the good solubility of these polymers in water and in organic solvents was of use. The reactions on the polymer were performed in the organic phase. To purify the starting monomers, which were used in excess, use was made of their water-solubility, associated with ultrafiltration. The monomers can so be separated. A big drawback of this method is the constant change of organic and aqueous phases and the long periods of time needed for ultrafiltration.

We have now found that the esters of amino acids and peptides with polyethylene glycol (PEG) or polypropylene glycol (PPG) can be extremely readily purified by crystallization from a suitable solvent, that is to say, above all freed from reactants used in excess, practically independently of the properties of the peptide portion.

The invention relates to a process for the preparation of peptides by the condensation of amino acids or peptides esterified with a free OH group of an optionally monoacylated or monoalkylated polyalkylene glycol having an average molecular weight of 2,000 to 40,000, the alkylene group of which contains 2 to 3 carbon atoms, with further amino acids or peptides, followed by cleavage of the peptide so obtained from the polymeric glycol. In particular, in the process, the peptide, while bound to the polymeric glycol, is purified at least once before it is cleaved therefrom, and/or in prior intermediate stages, by crystallization from organic solvents or mixtures thereof.

Suitable polymers that precipitate as crystals even when bound to longer peptide chains are above all, polyethers formed from ethylene glycol or propylene glycol. For smaller peptides, polymeric glycols having a low molecular weight, for example about 2,000 – 10,000, are preferably used. However, for the synthesis of moist peptides it is advantageous to use polymeric glycols having a higher molecular weight. Besides polyethylene and polypropylene glycols, monofunctional polymers can be used in which one of the hydroxy groups of the glycol is blocked by etherification or esterification.

The polyethers may be homopolymeric, that is contain the same glycols, namely polyethylene glycols (PEG) or polypropylene glycol (PPG), or they may also contain different glycols as basic units. It is essential that at least one hydroxyl or halogen grouping per molecule of polyether is present in addition to the ether grouping in order to be able to bind the amino acid.

The process of the invention is performed in such a manner that the first amino is bound, by esterification of a carboxy group thereof, with a functional group of the polyether, for example a hydroxyl or halogen group, according to known methods. The amino-acid-polyether ester is precipitated to form crystals by adding organic solvents under such conditions that excess amino acid or amino acid derivative and condensation agent remain in solution and can therefore be separated simply and rapidly. For example, the polymers can be precipitated as crystals with ether, preferably with diethyl ether or diisopropyl ether, or also with hydrocarbons, for example petroleum ether, from practically all suitable solvents. The solvents must, however, be miscible with the ethers or hydrocarbons. Such solvents are, for example: halogenated hydrocarbons, such as methylene chloride, chloroform or carbon tetrachloride; aromatic hydrocarbons, such as benzene, chlorobenzene, toluene, ethylbenzene or xylene; strongly polar solvents, such as dimethyl formamide, dimethyl sulfoxide or dimethyl acetamide; basic or acid solvents, such as pyridine, glacial acetic acid or trifluoroacetic acid; cyclic; ethers, such as tetrahydrofurane or dioxane, alcohols, such as methanol, ethanol, n-propanol, isopropanol, trifluoroethanol, methyl glycol or butyl glycol; esters, such as ethyl; acetate and ketones, such as acetone, methyl ethyl ketone and cyclohexanone or mixtures of these solvents.

The polymers can also be directly recrystallized from alcohols, such as methanol, ethanol, n-propanol, isopropanol or n-butanol; from ketones, such as acetone or methyl ethyl ketone; from and ethyl acetate or carbon tetrachloride; or from mixtures of these solvents.

The crystallization according to the invention needs not be performed after every reaction step. Sometimes, it is advantageous to choose another purification method instead of one of the crystallizations.

The reaction products precipitate in pure form and can be used promptly for the next reaction step. If desired, the crystallization can be repeated without any considerable loss of time.

The synthesis per se of the peptides does not differ from the usual operational method in a homogeneous phase. The individual reaction steps, the protective groups used, and the cleavage and condensation methods are described, for example, in Schroder-Lubke, The Peptides, New York 1964/65 and are the object of numerous synoptical papers more recently reported.

Amino acids can be coupled to the polymeric glycol according to any known method of peptide chemistry. To avoid racemization in the coupling of acyl peptides to the polymer, the methods advantageously used are those in which racemization is minimal. The coupling reactions are preferably performed in solvents, such as methylene chloride, chloroform, dimethyl formamide or pyridine.

All those protective groups that can be split off selectively with respect to the ester bond are suitable. For example carbobenzoxy radical can also be split off, in this case by catalytic hydrogenation, which is not possible with styrene resins as supports.

The peptide, synthesized stepwise or by fragmental coupling, can be split off from the polymer by alkaline hydrolysis, transesterification, ammonolysis or hydrazinolysis. When the peptide split off is water-insoluble, the polymeric glycol is dissolved with water and the peptide is filtered off. When the peptide split off is soluble in alcohol, the polymeric glycol can be precipitated with alcohol and the peptide can be obtained by concentrating the filtrate. When the peptide split off is water-soluble, methylene chloride or chloroform and water are used for separation. The peptide is put into water; the polyethylene glycol or the polypropylene glycol remain in the organic phase.

Further methods for the separation of the polymer supports are counter-current distribution, column chromatography and ultrafiltration.

It has been known that polyethylene glycol, for example, can have an about 60% helix structure confirming its crystalline ranges. However, it was a great surprise that compounds in which very different intermolecular actions occur, on account of their amino acid or peptide content, can especially readily and rapidly be precipitated as easily filtrable crystals from suitable solvents, independent of their peptide portion.

By proceeding in this manner, peptide synthesis in a homogeneous phase is no longer limited by the difficulty of purifying the products of the individual reaction steps in an easy manner. Heretofore, the peptides and their derivatives precipitated from the reaction medium almost always as smeary, resinic or oily products or contained contaminations when they precipitated in solid form.

A further advantage of the process of the invention is that peptides that normally are water-soluble, do not very much tend to crystallization, and cannot be purified by the usual separation methods between organic solvents solvent and aqueous solutions, now are easy to handle and to purify as esters of the polymers of the invention. Furthermore, a great number of peptides were difficult to dissolve, a problem that is now overcome by this method.

The advantages of the peptide synthesis in a homogeneous phase are fully maintained in the process of the invention, namely a high reaction rate, linear kinetics and easy reaction control.

When performed in accordance with the process of the invention, the peptide synthesis can be automated because all the reaction steps, including the separation of excess reactants, always occur in the same manner and without deviation due to the crystallization of the peptide polymer compounds according to the invention.

Expedient protective groups and condensation methods contribute to make a real high-speed process out of the process of the invention. For example, the Boc protective group is split off after about 10 – 15 minutes. Within the same period of time, excess solvent is eliminated and crystallization according to the invention occurs by adding an ether, such as diethyl or diisopropyl, ether and so does the separation by filtration.

The peptides prepared according to the process of the invention can be used as therapeutics or diagnostics or as intermediates for the preparation of other peptides valuable for therapy and diagnosis, such as, for example oxytocin, vasopressin, glucagon, secretin, ACTH, thyrocalcitonin, gastrin, TRH, LH-RH, substance P or insulin.

The following Examples illustrate the invention:

EXAMPLE 1

Synthesis of the tetrapeptide H-Leu-Ala-Gly-Val-OH on polyethyleneglycol (PEG) MW 2,000 a. Esterification of Boc-Val-OH with PEG (MW 2,000)

2 g of PEG (MW 2,000), 4.34 g of Boc-Val-OH and 4.12 g of DCCI (dicyclohexylcarbodiimide) were dissolved in 20 ml of $CH_2Cl_2$ and stirred for 7 days at room temperature with the exclusion of humidity. The precipitated DC (= dicyclohexyl)-urea was suction-filtered and the solution was condensed to about 10 ml, cooled to 0° to −10°C, and cold diethyl ether was added dropwise until Boc-Val-PEG had fully precipitated. The precipitate was suction-filtered, taken up in about 10 ml of $CH_2Cl_2$, and reprecipitated with ether at lower temperature (−10°C).

The precipitate was again suction-filtered and dried under reduced pressure.

Yield: 2.05 g of Boc-Val-PEG capacity 70%, resp. 0.7 mM/g (aminoacid analysis).

The protective group (Boc) is split off by treating Boc-Val-PEG with 20 ml of a mixture of $CH_2Cl_2$ and trifluoroacetic acid (TFA) (1:1) for 20 minutes at room temperature, condensing the solution on the rotary evaporator (to about 5 ml) and precipitating H-Val-PEG by adding cold ether draperies. The precipitate was suction-filtered, taken up in a small amount of $CH_2Cl_2$, reprecipitated with ether and the residue was dried under reduced pressure.

Yield: 2.00 g of H-Val-PEG · TFA.

b. Peptide Synthesis 2.0 g of H-Val-PEG · TFA (1.4 mM) were dissolved in 20 ml of $CH_2Cl_2$ (I). 2.8 mM of DCCI were slowly added dropwise, at 0°C in a separate vessel, to a solution of 5.6 mM of Boc-Gly-OH in 10 ml of $CH_2Cl_2$. After about 30 minutes at 0°C, the DC-urea obtained was suction-filtered and the clear solution (Boc-aminoacid anhydride) was added to solution I. Thereafter, 1.5 mM of N-methylmorpholine were slowly added dropwise and the reaction solution was stirred at room temperature for 30 minutes. Condensing to 10 ml followed and the polymer peptide was precipitated at −10°C, by adding dropwise diethyl ether. The solution was stirred for about 10 minutes at −10°C, the precipitate was suction-filtered and dried under reduced pressure.

By treating Boc-Gly-Val-PEG with $TFA/CH_2Cl_2$ (1:1), the protective group was split off.

After working up in the manner described under (a) the yield was 1.98 g of H-Gly-Val-PEG · TFA. In the same manner, H-Gly-Val-PEG · TFA was reacted with 2.8 mM of Boc-Ala-anhydride. After splitting off the protective group and precipitating with ether, 1.96 g of H-Ala-Gly-Val-PEG · TFA were obtained. By reacting correspondingly H-Ala-Gly-Val-PEG · TFA with Boc-Leu-anhydride (1.8 mM), 1.95 g of Boc-Leu-Ala-Val-PEG were obtained. The aminoacid analysis of a hydrolyzed sample of that substance showed the following amino acid ratio:

Val: Gly: Ala: Leu = 1.00: 1.01: 0.99: 1.01 c. Splitting off and isolating peptide

A solution of 1.0 g of Boc-Leu-Ala-Gly-Val-PEG in 10 ml $H_2O$/dioxane (1:1) and 1.5 ml of 1 N KOH was stirred for 1 hour at room temperature. It was adjusted to the exact neutral pH with 1.5 ml of 1 N HCl and evaporated to dryness. To eliminate the salts, the residue was digested twice with 20 ml of $CH_2Cl_2$ and the insoluble KCl was filtered off. The $CH_2Cl_2$ was extracted, the residue was taken up in 20 ml of absolute ethanol and cooled to −10°C for 2 hours. The precipitate formed (PEG) was separated by centrifuging at 15,000 r/min, the supernatant solution was decanted off and the residue was taken up in ethanol, cooled and again centrifuged. The combined solutions of ethanol were condensed to 10 ml and allowed to stand over night at −10°C. The precipitate (slight turbidity) was suction-filtered and the filtrate was evaporated to dryness. The Boc-tetra-peptide (275 mg) was treated with 10 ml of $TFA/CH_2Cl_2$ to split off the Boc-protective group and the solvent was extracted under reduced pressure. The residue was taken up in $H_2O$, the solution was treated with slightly basic ion exchanger at pH 6 and lyophilized after filtering off the exchanger. The yield was 202 mg, correct amino acid analysis.

EXAMPLE 2

Synthesis of the tetrapeptide H-Leu-Ala-Gly-Val-OH on polypropylene glycol (PPG)

a. Esterification of Boc-Val-OH with PPG (MW 6000) and splitting off the protective group 5.0 g of PPG (MW 6,000), 4.34 g of Boc-Val-OH (= 20 mM) and 4.12 g of DCCI were dissolved in 50 ml of $CH_2Cl_2$ and stirred during 7 days at room temperature with the exclusion of humidity, whereafter the solution was worked up as is described in example 1a).

Yield: 5.0 g of H-Val-PEG · TFA.

Capacity 0.3 mMg (amino acid analysis).

b. Peptide synthesis 5.0 g of H-Val-PPG · TFA were reacted in the manner described in example 1b) with 3mM of Boc-Gly-anhydride, Boc-Ala-anhydride and Boc-Leu-anhydride. After the last coupling (Boc-Leu), 4.7 g of Boc-Leu-Ala-Gly-Val-PPG were obtained.

Result of amino acid analysis: Val:Gly:Ala:Leu = 1.00: 0.00: 0.99: 1.02.

c. Splitting off and isolating the peptide

To split off the peptide, a solution of 4.0 g of Boc-Leu-Ala-Gly-Val-PPG was stirred for two hours at room temperature in 40 ml of $H_2O$/dioxane (1:1) and 2 ml of 1 N KOH. After neutralization with 2 ml 1 N HCl, the peptide was isolated in the same manner as described in Example 1c).

The yield of crude tetrapeptide was 410 mg. The peptide portion in the crude tetrapeptide was 68% (amino acid analysis), that is a total amount of 65%, calculated on Val.

The result of amino acid analysis was: Val: Gly: Ala: Leu = 1.00: 1.01: 0.99: 1.00.

In a comparison made in thin-layer chromatography with the tetra-peptide synthesized in Example 1 the product showed an identical behaviour.

EXAMPLE 3

Synthesis of Arg-Pro-Lys-Pro-Gln-Gln-Phe-Phe-Gly-Leu-Met ("substance P") on PEG (MW 15,000)

a. Esterification of Boc-Met-OH with PEG (MW 15,000)

7.50 g of PEG (MW 15,000) (= 1 mM of functional groups), 10 mM of Boc-Met-OH and 10 mM of DCCI were dissolved in 50 ml of $CH_2Cl_2$ and stirred for 7 days, at room temperature, with the exclusion of humidity. Then, the solution was filtered off, condensed to about 20 ml, cooled to −10°C and the Boc-Met-PEG was precipitated, while stirring, by adding cold diethyl ether dropwise. The mixture was stirred at −10°C for another 10 minutes, the precipitate was suction-filtered with a glass frit and dried under reduced pressure. The white powder was again dissolved in 30 ml of $CH_2Cl_2$ and precipitated with ether as described above. After filtering off and drying the precipitate, 7.50 g of Boc-Met-PEG were obtained. Capacity after aminoacid analysis: 0.08 mM/g, resp. 60% of the theory.

b. Peptide synthesis 7.00 g of H-Met-PEG · TFA (= 0.56 mM) were dissolved in 70 ml of $CH_2Cl_2$ (solution I). In a separate vessel, 2.3 mM of Boc-Leu-OH were dissolved in a small amount of $CH_2Cl_2$, cooled to 0°C and 1.15 mM of DCCI were added. After stirring for 30 minutes at 0°C, the mixture was added to solution I by filtering off the precipitated DC-urea. Thereafter, 0.60 mM of M-methylmorpholine were slowly added dropwise to the reaction mixture and the clear solution was allowed to stand for 30 minutes. The solution was condensed to about 30 ml under reduced pressure, cooled to −10°C and diethyl ether was slowly added dropwise while stirring thoroughly (about 200 ml), until the polymer peptide had precipitated quantitatively. The mixture was again stirred for 10 minutes at −10°C and then the precipitate was suction-filtered over a glass frit. To eliminate the excess Boc-amino acid, the polymer peptide was again taken up in a slight amount of $CH_2Cl_2$ (about 30 ml) and precipitated with ether as described above. The precipitate was suction-filtered and dried under reduced pressure.

Yield: 6.98 g of Boc-Leu-Met-PEG.

The protected polymer peptide was dissolved in a mixture of $TFA/CH_2Cl_2$ (1:1) (10% solution) and stirred for 20 minutes at room temperature. The solution was condensed (to about 30 ml) and the polymer peptide was precipitated with diethyl ether while cooling to −10°C and stirring thoroughly. After suction-filtering and drying, the residue was taken up in about 30 ml of $CH_2Cl_2$ and precipitated with ether.

The white powder was suction-filtered again and dried under reduced pressure until its weight remained constant.

Yield: 6.95 g of H-Leu-Met-PEG · TFA.

In the manner described above, the following aminoacid derivatives were coupled successively (equal quantitative ratios):

A. Boc-Gly-OH: Yield of H-Gly-Leu-Met-PEG · TFA = 6.98 g b. Boc-Phe-OH: Yield of H-Phe-Gly-Leu-Met-PEG · TFA = 6.93 g c. Boc-Phe-OH: Yield of Phe-Phe-Gly-Leu-Met-PEG · TFA = 6.92 g d. Boc-Gln-OH: This product was synthesized with the following alternations:

Boc-Gln-OH was dissolved in a mixture of $DMF/CH_2Cl_2$ (1:2).

The activation time for the preparation of Boc-Gln-anhydride was only 5 minutes. DC-urea that precipitated afterwards was suction-filtered after coupling had completed. To eliminate the excess Boc-Gln-OH quantitatively, the protected polymer peptide was dissolved in absolute ethanol while heating (10% solution) after precipitating twice with diethyl ether and allowed to cool. After about 2 hours at −5°C, the precipitate was isolated by centrifuging (30 minutes at 10,000 r/min) and decanting the supernatant and dried. Thin-layer chromatography showed that all the excesses were eliminated. The Boc-group was split off by treating it for 10 minutes with $TFA/CH_2Cl_2$ at 0°C. Then, the peptide polymer was precipitated directly from the solution with ether. Yield of H-Gln-Phe-Phe-Gly-Leu-Met-PEG · TFA = 6.88 g.

e. Boc-Gln-OH: The same procedure took place as described under d).

Yield of H-Gln-Gln-Phe-Phe-Gly-Leu-Met-PEG · TFA = 6.70 g.

To dissolve the polymer peptide, 20% of DMF were added to the $CH_2Cl_2$ from that stage.

f. Boc-Pro-OH: Yield of H-Pro-Gln-Gln-Phe-Phe-Gly-Leu-Met-PEG · TFA = 6.60 g.

g. Boc-Lys(Z)-OH: Yield of H-Lys(Z)-Pro-Gln-Gln-Phe-Phe-Gly-Leu-Met-PEG · TFA = 6.57 g h. Boc-Pro-OH: Yield of H-Pro-Lys(Z)-Pro-Gln-Gln-Phe-Phe-Gly-Leu-Met-PEG · TFA = 6.25 g i. Z-Arg(Tos)-OH: The excess amounts were eliminated as described under d). Yield of Z-Arg(Tos)-Pro-Lys(Z)-Pro-Gln-Gln-Phe-Phe-Gly-Leu-Met-PEG = 6.05 g.

c. Splitting off and isolating the peptide

To split off the fully protected peptide from the support by ammonolysis, 4.0 g of polymer peptide were dissolved in 40 ml of absolute ethanol and 20 ml of $CH_2Cl_2$. The solution was saturated at $-10°C$ for about 30 minutes with ammonia (using a pressure bottle) and allowed to stand for 4 days at room temperature. Then, the solvent was distilled off and the solid residue was digested with 40 ml of $H_2O$ (pH 5). The water-insoluble peptide was centrifuged (for 30 minutes at 15,000 r/min). The supernatant solution was decanted and treated with about 20 ml of $H_2O$.

After repeating centrifugation, decantation and lyophilization, 520 mg of crude peptide were obtained.

Yield: 520 mg of "substance P", fully protected.

The IR-spectrum of the peptide shows that the polymer was eliminated quantitatively.

Splitting off the protective groups:

220 mg of fully protected peptide were treated at 0°C for 1 hour with HF (by adding 2 ml of anisol) the HF was eliminated (using $N_2$-current) and dried in an exsiccator. The residue was extracted with 30 ml of ethyl acetate and 0.1 N acetic acid. The ethyl acetate phase was extracted three times with $H_2O$ and the aqueous phases were combined. After lyophilizing twice, 180 mg of crude peptide were obtained.

Yield: 180 mg of "substance P".

Capacity of the polymer after the last synthesis cycle: 55% (calculated on Met).

Yield upon splitting off by ammonolysis: 90% of the theory (amino-acid analysis).

d. Purification and characterization of the peptide

The synthesized crude product showed four ninhydrinpositive bands at pH 1.9 as demonstrated by a proper chromatography. The product was purified and desalted by a continuous high-tension electrophoresis in a free buffer film at pH 1.9 (electrolyte: 14.5 ml concentrated formic acid and 11.9 ml of glacial acetic acid in 5,000 ml of water). The field intensity was about 35 V $cm^{-1}$. About 100 mg of crude product were dissolved in 5 ml of buffer and led in on the anode (over glass a tube). The fraction division was ascertained by dot samples with ninhydrin and Sakaguchi as well as by direct paper electrophoreses with concentrated aliquote small samples taken from the individual glass tubes. The pooled fractions indicated below were lyophilized twice with water:

Fraction 27 – 33: about 25 mg of white, highly hygroscopic powder that corresponds to pure substance P according to the tests made so far.

Fraction 35 – 39: Pure side component comprising the electrophoretic motility of 0.69 x Lys.

The total yield of pure "substance P" was about 35% of the theory calculated on the C-terminal Met used.

EXAMPLE 4

Synthesis of the tripeptide Pyroglu-His-Pro-$NH_2$(TRH) on PEG (MW 6,000)

a. Esterification of PEG 6 g of PEG (MW 6,000) (= 2 mM of OH-groups), 10 mM of Boc-Pro-OH and 10 mM of DCCI were dissolved in 60 ml of $CH_2Cl_2$ and stirred for 7 days, at room temperature, with the exclusion of humidity. The DC-urea was suction-filtered and 5 mM of Boc-Pro-anhydride were added to the solution (separate preparation of anhydride with DCCI in a manner analogous to that described in Examples 1 - 3).

The homogeneous solution was heated under reflux for 12 hours, condensed to about 20 ml and Boc-Pro-PEG was precipitated by adding about 200 ml of ether dropwise. After suction-filtering the precipitate, the product was again taken up in 20 ml of $CH_2Cl_2$ and reprecipitated with ether. To split off the Boc-group, the dried residue was dissolved in 60 ml of a mixture of $TFA/CH_2Cl_2$ (1:1) and allowed to stand at room temperature for 20 minutes. Then, the trifluoroacetic acid was extracted under reduced pressure and ether was added dropwise to the condensed solution until H-Pro-PEG · TFA had fully precipitated. After suction-filtering, taking up in $CH_2Cl_2$, reprecipitating with ether and drying the precipitate, 5.98 g of H-Pro-PEG · TFA were obtained.

Capacity 0.17 mM/g (aminoacid analysis) = 51 % of the theory.

b. Fragment coupling 3 g of H-Pro-PEG · TFA (= 0.5 mM) were dissolved in a mixture of 10 ml of $CH_2Cl_2$ and 10 ml DMF, cooled to $-30°C$ and neutralized with 0.55 mM of N-methylmorpholine.

280 mg = 1 mM of Pyroglu-His-$N_2H_3$ were dissolved at 0°C in a mixture of 5 ml of DMSO, 5 ml of DMF and 2.5 ml of 2,4 N HCl/tetrahydrofurane, cooled to $-20°C$. 0.2 ml of isoamylnitrite were added, and the mixture was stirred for 30 minutes at $-20°C$ and neutralized by adding 0.85 ml of triethyl amine. That mixture was added to the H-Pro-PEG solution also cooled to $-30°C$. The reaction mixture was stirred below 0°C for 30 minutes and at 4°C for 12 hours, then evaporated to dryness under reduced pressure and taken up in 30 ml of absolute methanol while heating. The clear solution was allowed to stand at 4°C for 2 hours and at $-10°C$ over right crystallization the PEG-peptide and was then centrifuged from the precipitated PEG peptide at $10^4$ r/min. The supernatant solution was decanted, the residue was again taken up in methanol, the PEG peptide was reprecipitated at low temperature and worked up.

Yield: 2.85 g of Pyroglu-His-Pro-PEG.

The product had an amino acid ratio of Pro-Glu = 1.00:0.71.

To repeat fragment condensation, the product was dissolved in 20 ml of $CH_2Cl_2$, neutralized with N-methylmorpholine and reacted with 280 mg = 1 mM of Pyroglu-His-$N_2H_3$ as has been described above. After working up the reaction product, 2.70 g of Pyroglu-His-Pro-PEG were recovered. The amino acid ratio of a hydrolized sample was Pro:Glu = 1.00:1.00 c. Splitting off by ammonolysis 2.5 g of Pyroglu-His-Pro-PEG were dissolved in a mixture of 50 ml of MeOH and 25 ml of $CH_2Cl_2$. The solution was saturated with $NH_3$ at $-10°C$ and allowed to stand at room temperature for 4 days. The product was evaporated to dryness, the residue was dissolved in 50 ml of MeOH and the PEG was precipitated over night, after cooling the solution to 0°C. The precipitate was centrifuged, again treated with MeOH and recrystallized in a manner analogous to that of the PEG above. The combined methanol solutions were evaporated to dryness, the crude peptide was taken up in a slight amount of water and, to eliminate the last traces of PEG, the product was separated by chromatography with Sephadex (G 15) over a column (2,5 × 120 cm). After evaporating the water, the combined tolidine-positive fractions yielded 115 mg of Pyro-glu-His-Pro-NH$_2$, which corresponded to a yield of 71% of the theory, calculated on Pro before splitting off. The total yield of the synthesis, calculated on the first amino acid (Pro), was 64% of the theory.

The aminoacid ratio of the products so obtained was Pro:His:Glu = 1.00: 0.96: 0.99. The behavior of that material as shown by thin layer chromatography correspond to that of the Pyroglu-His-Pro-NH$_2$ that was prepared in the classical way with the same coupling being made.

EXAMPLE 5

Synthesis of the tetrapeptide H-Leu-Ala-Gly-Val-OH on PEG 20,000

20 g of H-Val-PEG (MW 20,000) (esterification as described in Example 1, capacity 85% of the theory = 0.085 mM/g), were dissolved in 100 ml of CH$_2$Cl$_2$, 1.9 mM of triethyl amine and 5.0 mM of Z-Gly-ONP were added, and the solution was stirred for 24 hours at room temperature. The solution was condensed to about 40 ml and precipitated twice with diethyl ether. The residue was dissolved in 300 ml of methanol after suction-filtering on a glass frit. 2.5 ml of 4 N HCl/MeOH and Pd/C were added and the solution was hydrogenated at room temperature and under normal pressure until the hydrogen absorption had stopped.

The catalyst was filtered off, the filtrate was condensed and diethyl ether was added to it. The crystallized polymer peptide was dried until weight constancy. Yield: 19.3 g of H-Gly-Val-PEG.

In an analogous manner H-Gly-Val-PEG was firstly reacted with Z-Ala-ONP and then with Z-Leu-ONP. After drying, 18.5 g of H-Leu-Ala-Gly-Val-PEG were obtained. The amino acid analysis showed the following ratio:

Val: Gly: Ala: Leu = 1.00: 0.95: 0.99: 0.99

EXAMPLE 6

Synthesis of the tetrapeptide H-Leu-Ala-Gly-Val-OH on PEG (MW 2,000) after blocking residual hydroxyl groups on PEG In an analogous manner to Example 1, 2 g of PEG (MW 2,000), 4.34 g of Boc-Val-OH and 4.12 g of DCCI were dissolved in 20 ml of CH$_2$Cl$_2$ and stirred at room temperature for seven days.

Then, the precipitated DC urea was suction-filtered and 20 mM of acetanhydride were added to the clear filtrate. The solution was boiled under reflux for 4 hours, condensed to about 10 ml and worked up as described in Example 1.

The peptide synthesis was carried out as described in Example 1. After splitting off and isolating the peptide, the same yield and the same amino acid composition were obtained as in Example 1.

What we claim is:

1. In a process for synthesizing a peptide in a liquid phase by at least once forming a peptide bond between a carboxy group of an amino acid or peptide and an amino group of an amino acid or peptide, which latter amino acid or peptide has a carboxy group bound by an ester bond to an hydroxy group of a polymer which is
   a. a polyalkylene glycol, the alkylene group of which has 2 or 3 carbon atoms, or
   b. such a polyalkylene glycol which has been mono-esterified or mono-etherified, whereby a new polymer-bonded peptide is formed, and then cleaving said ester bond at the conclusion of the synthesis, the improvement wherein said polymer has a molecular weight between 2000 and 40000 and wherein, prior to cleavage of said ester bond, said polymer-bound peptide is crystallized at least once during the synthesis to separate it from said liquid phase.

2. A process as in claim 1 wherein a plurality of peptide bonds are formed in a plurality of sequential steps during the peptide synthesis and wherein the new polymer-bound peptide formed in each of the sequential steps is separated from said liquid phase by crystallization.

* * * * *